United States Patent [19]

Kozin et al.

[11] Patent Number: 4,759,370
[45] Date of Patent: Jul. 26, 1988

[54] OPHTHALMOTONOMETER

[75] Inventors: Mikhail P. Kozin; Jury I. Sakharov, both of Kuibyshev; Svyatoslav N. Fedorov, Moscow, all of U.S.S.R.

[73] Assignee: Kuibyshevsky politekhnitchesky Institute Moskov Nauchno-issledovatelsky Institute Mikrokhirurgii glaza, Moscow, U.S.S.R.

[21] Appl. No.: 17,770

[22] Filed: Feb. 20, 1987

[30] Foreign Application Priority Data

Feb. 25, 1986 [SU] U.S.S.R. ............... 4023145

[51] Int. Cl.$^4$ ............................................... A61B 3/16
[52] U.S. Cl. ................................... 128/645; 128/652
[58] Field of Search ................ 128/645, 650, 651, 652

[56]  References Cited

U.S. PATENT DOCUMENTS 3,992,926  11/1976  Berryhill ......................... 128/652
4,164,863  8/1979  Ragsdale ........................ 128/652
6,572,319  3/1971  Bilther et al. ................. 128/645 X Primary Examiner—Edward M. Coven
Attorney, Agent, or Firm—Lilling & Greenspan

[57] ABSTRACT

The ophthalmotonometer of the invention comprises a frequency-output transducer of linear motions which correspond to intraocular pressure; a reference-frequency generator; a frequency comparator whose inputs are connected to the outputs of the frequency-output transducer and of the reference-frequency generator, a difference-frequency divider connected to outputs of the frequency comparator; a circuit for measurement of the cycle of difference-frequency oscillations connected to outputs of the reference frequency generator and the frequency divider, said cycle corresponding to intraocular pressure in millimeters of mercury; and a measurement results registration circuit connected to outputs of the cycle measurement circuit.

1 Claim, 5 Drawing Sheets

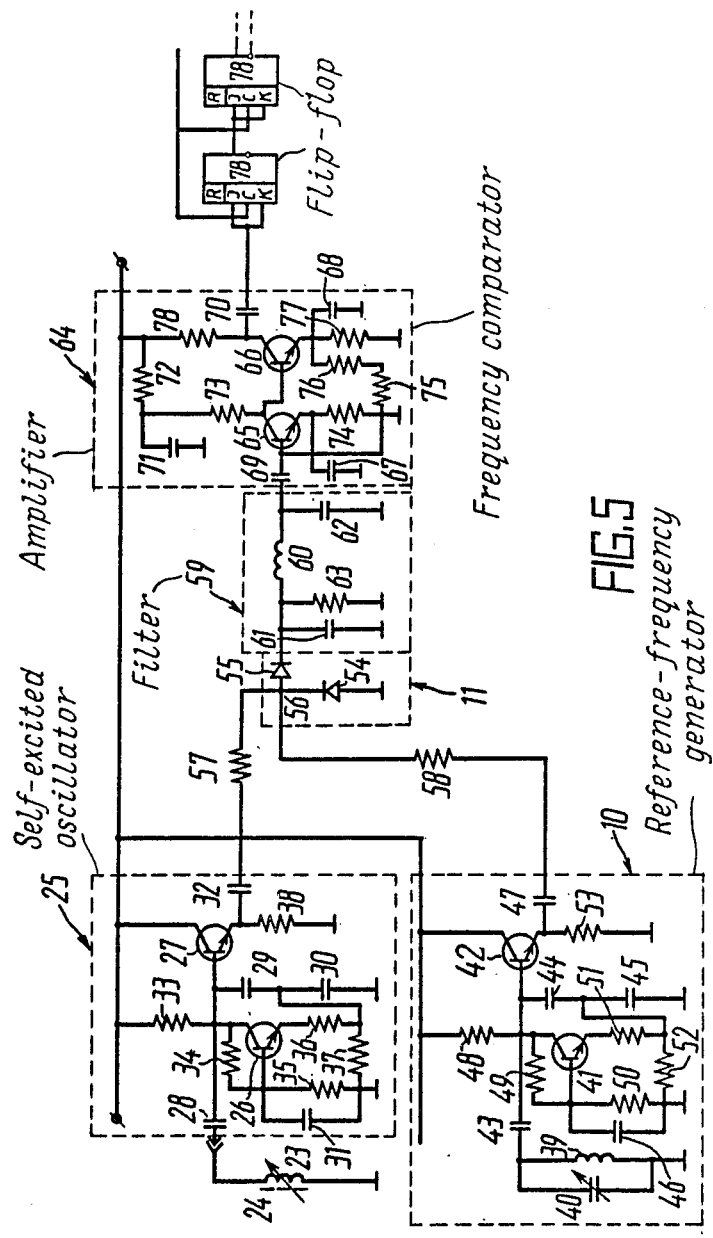

OPHTHALMOTONOMETER

FIELD OF THE INVENTION

This invention relates generally to medical apparatus and more specifically it concerns ophthalmotonometers.

The invention is applicable in ophthalmology for diagnosis and control over the treatment coursing of eye diseases under clinical and outpatient conditions.

BACKGROUND OF THE INVENTION

Known in the present state of the art are impression tonometers and tonographs that measure intraocular pressure in conventional units, one such unit corresponding to a diaplacement of 50 µm. The readings taken in conventional units are translated into millimeters of mercury by means of special conversion tables or through the use of a computing device, which is more convenient in medical practice (cf. SU A 135,583, SU A 294,608, SU A 1,044,272). However, additional computation extends the patient's servicing time, while incorporation of computing devices sophisticates construction of such tonometers.

In addition, the aforesaid conversion and computation involves errors due to stepwise arranged numerical data in special conversion tables so that the data increments substantially increase within the domain of low values of the measured pressure expressed in conventional units.

The technical solution closest to the present invention is a high-frequency tonometer for measuring and recording the intraocular pressure, comprising a frequency-output linear-motion transducer, said motions corresponding to intraocular pressure expressed in conventional units, and a recording instrument. The transducer incorporates a plunger which is traversable with respect to the casing so as to change its position relative to the inductors accommodated in the transducer casing. The transducer output frequency is proportional to the length of the plunger travel with respect to the transducer casing and is converted into a d.c. signal which is taken down by the recording instrument. Then the pressure measured in the conventional units is represented in millimeters of mercury by the conversion technique described above (cf. SU A 119,651).

However, making use of a special conversion table involves interpolation of the tabulated numerical data, while application of a special computing unit complicates substantially the entire tonometer. Moreover, the initial section, according to which intraocular pressure is as a rule estimated, is featured in a majority of cases by the widely variable displacement values, which are to be averaged. The data averaging procedure is usually performed by the operator in the course of data processing, which affects adversely the effectiveness and accuracy of measurements.

The invention is aimed at the provision of an ophthalmotonometer which would be capable of measuring intraocular pressure directly in millimeters of mercury.

SUMMARY OF THE INVENTION

It is an object of the invention to provide an ophthalmotonometer which would be capable of measuring intraocular pressure directly in millimeters of mercury.

It is another object of the invention to render an operator's work more efficient.

It is one more object of the invention to provide higher measurement accuracy.

The objects mentioned above are accomplished by an ophthalmotonometer, comprising a frequency-output linear-motion transducer, said linear motions corresponding to intraocular pressure, and a circuit for registration of the measurement results, said circuit being interconnected with the frequency-output linear-motion transducer according to the invention, the ophthalmotonometer also comprises a reference-frequency generator; a frequency comparator to one of whose inputs is connected the output of the reference-frequency generator, while connected to the other input thereof is the output of the frequency-output linear-motion transducer; a difference-frequency divider connected to the output of the frequency comparator; and a circuit for measuring the cycle of the difference-frequency oscillations, there being connected to one of the inputs of said circuit the ouput of the difference-frequency divider, while connected to the other input thereof is the output of the reference-frequency generator. The signal appearing at the output of the aforesaid circuit and corresponding to intraocular pressure in millimeters of mercury is then applied to the input of the measurement result registering circuit.

The ophthalmotonometer proposed herein makes it possible to dispense with the use of special conversion tables for determining intraocular pressure, is simple in construction and provides for an adequate accuracy of intraocular pressure measurement.

BRIEF DESCRIPTION OF THE DRAWINGS

Other objects and advantages of the present invention will hereinafter become more apparent from a consideration of the disclosure of some exemplary embodiments thereof with due reference to the accompanying drawings, wherein:

FIG. 5 is an electric diagram of an ophthalomotonometer, according to the invention.

DETAILED DESCRIPTION OF THE INVENTION

The construction and operation of the herein-disclosed ophthalmotonometer is based on the heretobefore-known intraocular pressure measurement technique, the pressure measured being expressed in conventional units (the so-called Schiotz' units).

Figure 1:
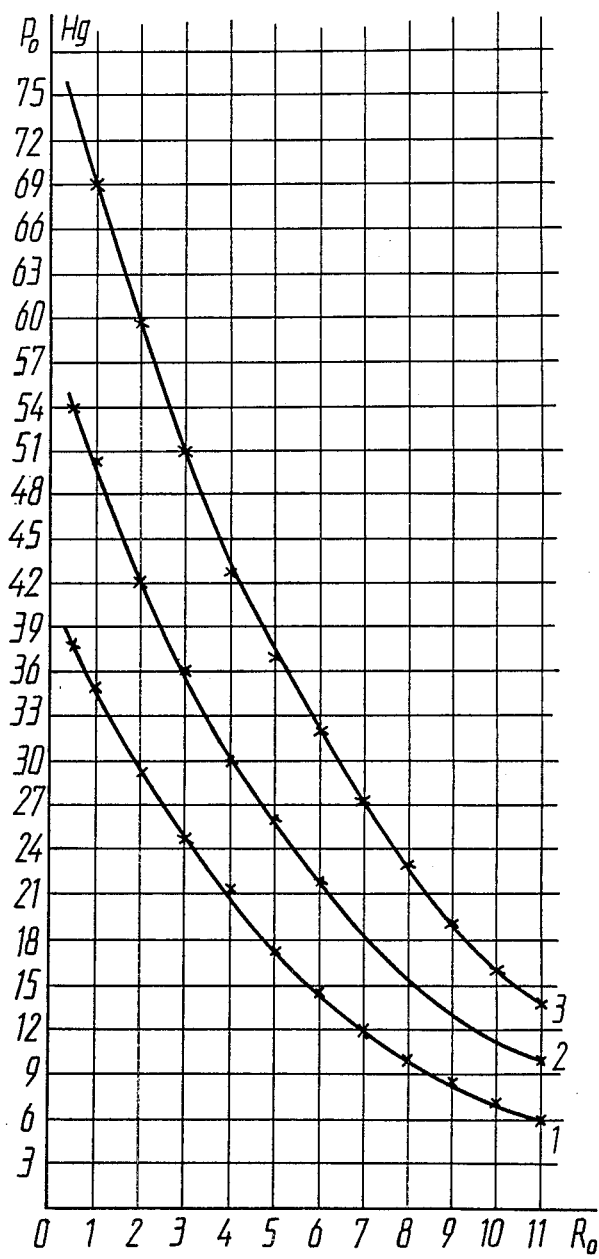
FIG. 1 is a graph, showing characteristic curves of the values of intraocular pressure versus the length of the plunger displacement, expressed in conventional units.

FIG. 1 represents the curves characteristic of the intraocular pressure value $P_o$ in millimeters of mercury versus the length $R_o$ of the transducer plunger displacement. The curve 1 corresponds to the plunger weight G of 5.5 g, the curve 2 corresponds to the weight of 7.5 g, and the curve 3 correpsonds to the weight of 10 g.

The values of $P_o$, as well as design values of the coefficient $$A_i = R_o P_o \qquad (1)$$

are tabulated in Table I.

TABLE I

| No. | $R_o$ | Conventional units | 1 | 2 | 3 | 4 | 5 | 6 | 7 | 8 | 9 | 10 | 11 |
|-----|-------|--------------------|---|---|---|---|---|---|---|---|---|----|----|
| 1 | 2 | 3 | 4 | 5 | 6 | 7 | 8 | 9 | 10 | 11 | 12 | 13 | 14 |
| 1 | G = 5.5 g | $P_o$, mm Hg | 35 | 29 | 25 | 21 | 17 | 14.5 | 12 | 10 | 8.5 | 7 | 6 |
| 2 | | $A_i = P_o R_o$ | 35 | 58 | 75 | 84 | 85 | 87 | 84 | 80 | 76.5 | 70 | 66 |
| 3 | | $P_{o1}$, mm Hg | 72.8 | 36.4 | 24.25 | 18.2 | 14.55 | 12.13 | 10.4 | 9.09 | 8.08 | 7.28 | 6.6 |
| 4 | | $\delta$, % | 108 | 25.5 | 3 | 8.6 | 14.4 | 16.3 | 13.3 | 9.1 | 4.9 | 4 | 10 |
| 5 | | $P_{o2}$, mm Hg | 78.3 | 39.15 | 26.1 | 19.6 | 15.66 | 13.1 | 11.2 | 9.79 | 8.7 | 7.83 | 7.118 |
| 6 | | $\delta_1$, % | 123.7 | 35 | 4.4 | 6.79 | 7.88 | 10 | 6.78 | 2.12 | 2.35 | 11.8 | 18.6 |
| 7 | G = 7.5 g | $P_o$, mm Hg | 50 | 45 | 36 | 30 | 26 | 22 | 18 | 15.5 | 13 | 11 | 10 |
| 8 | | $A_i = P_o R_o$ | 50 | 84 | 108 | 120 | 130 | 132 | 126 | 124 | 117 | 110 | 110 |
| 9 | | $P_{o1}$, mm Hg | 110.1 | 55 | 36.7 | 27.5 | 22.0 | 18.35 | 15.3 | 13.76 | 12.23 | 11.01 | 10.01 |
| 10 | | $\delta$, % | 120.2 | 31 | 1.94 | 8.33 | 15.3 | 16.5 | 12.6 | 11.2 | 5.9 | 0.09 | 0.1 |
| 11 | | $P_{o2}$, mm Hg | 118.8 | 59.4 | 39.6 | 29.7 | 23.7 | 19.8 | 17.0 | 14.85 | 13.2 | 11.9 | 10.8 |
| 12 | | $\delta_1$, % | 137.6 | 41.4 | 10 | 1.0 | 8.6 | 10 | 5.7 | 4.2 | 1.54 | 8 | 8 |
| 13 | G = 10 g | $P_o$, mm Hg | 69 | 59 | 51 | 43 | 37 | 32 | 27 | 23 | 19.5 | 16 | 14 |
| 14 | | $A_i = P_o R_o$ | 69 | 118 | 153 | 172 | 185 | 192 | 189 | 184 | 175.5 | 160 | 154 |
| 15 | | $P_{o1}$, mm Hg | 159.2 | 79.6 | 53.07 | 39.8 | 31.8 | 26.5 | 22.7 | 19.9 | 17.7 | 15.9 | 14.47 |
| 16 | | $\delta$, % | 13.07 | 34.9 | 4.05 | 7.46 | 14.05 | 17.2 | 15.9 | 13.4 | 4.2 | 0.5 | 3.36 |
| 17 | | $P_{o2}$, mm Hg | 172.8 | 86.4 | 57.6 | 43.2 | 34.6 | 28.8 | 24.7 | 21.6 | 19.2 | 17.3 | 15.7 |
| 18 | | $\delta_1$, % | 150.4 | 46.4 | 12.94 | 0.46 | 6.59 | 10 | 8.5 | 6.09 | 1.54 | 8 | 12.2 |

Table 1 contains the tabulated values of $P_o$ and the design values of the coefficient $A_i = P_o R_o$. Found therein are also design values of intraocular pressure $P_{o1}$ obtained from the following relation:

$$P_{o1} = A_o R_o, \qquad (2)$$

where $$A_o = \sum_{i+1}^{11} \frac{A_i}{11}, (i = 11).$$

The aforesaid Table contains design values of intraocular pressure measurement error $\delta$ by Eq (2)

$$\delta = \frac{100(P_{o1} - P_o)}{P_o} \% \qquad (3)$$

Figure 2:
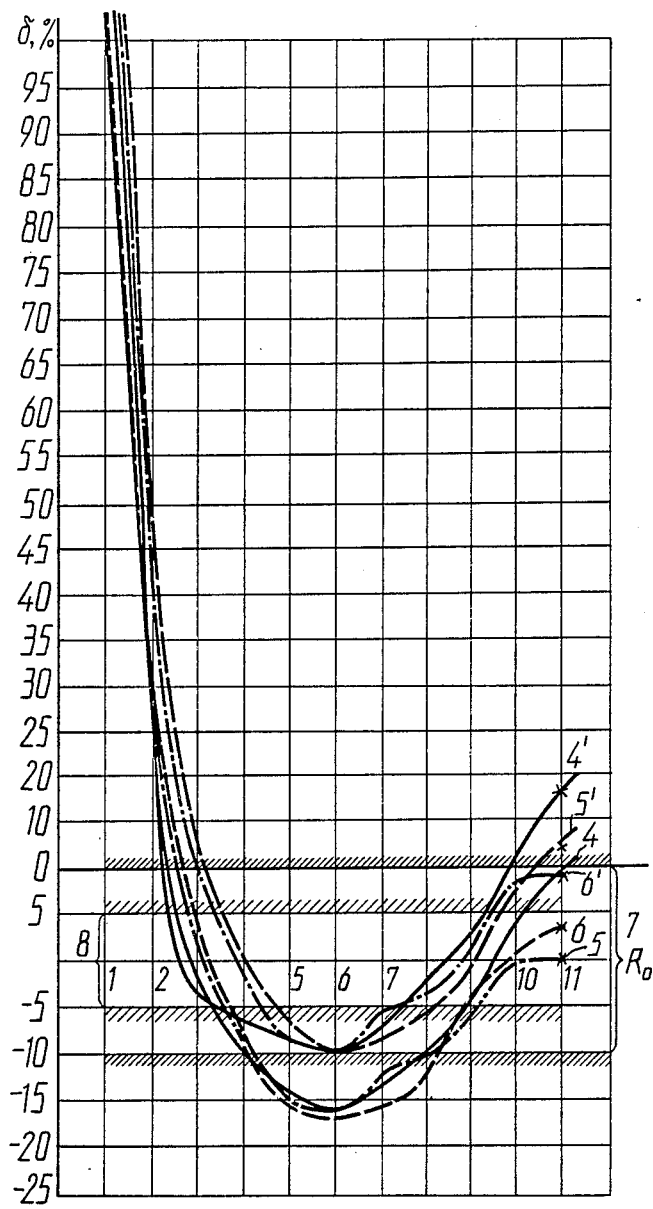
FIG. 2 is a graph, illustrating graphic representations of changes in measurement error versus intraocular pressure as measured in conventional units.

FIG. 2 represents graphic charts 4, 5, 6 showing changes in the value $\delta$ of the measurement error versus the intraocular pressure $P_o$ being measured, expressed in conventional units for the weight G equal to 5.5, 7.5, and 10 g. The same FIGURE illustrates also a 10-percent margin 7 of error, which is adopted as such to suit a required intraocular pressure measurement accuracy high enough for clinical studies.

The graphic charts 4, 5 and 6 are so replotted as to correspond to the value of the coefficient $A_2$ that satisfies the condition, wherein an extreme (mathematical) value $\delta$ of error equals 10 percent. As a result, new reconstructed graphic charts $4^1$, $5^1$, $6^1$ are obtained. Table 1 gives design values of $P_{o2}$ calculated by the formula $$P_{o2} = A_2 / R_o \qquad (2^I)$$

and the corresponding error values of $\delta_2$, which is calculated by the formula $$\delta = 100 \frac{P_{o2} - P_o}{P_o} (\%) \qquad (3^I)$$

As it is evident from FIG. 2, the values of $R_o$ from 3 to 10 conventional units fall within the 10-percent margin 7 of error.

Figure 3:
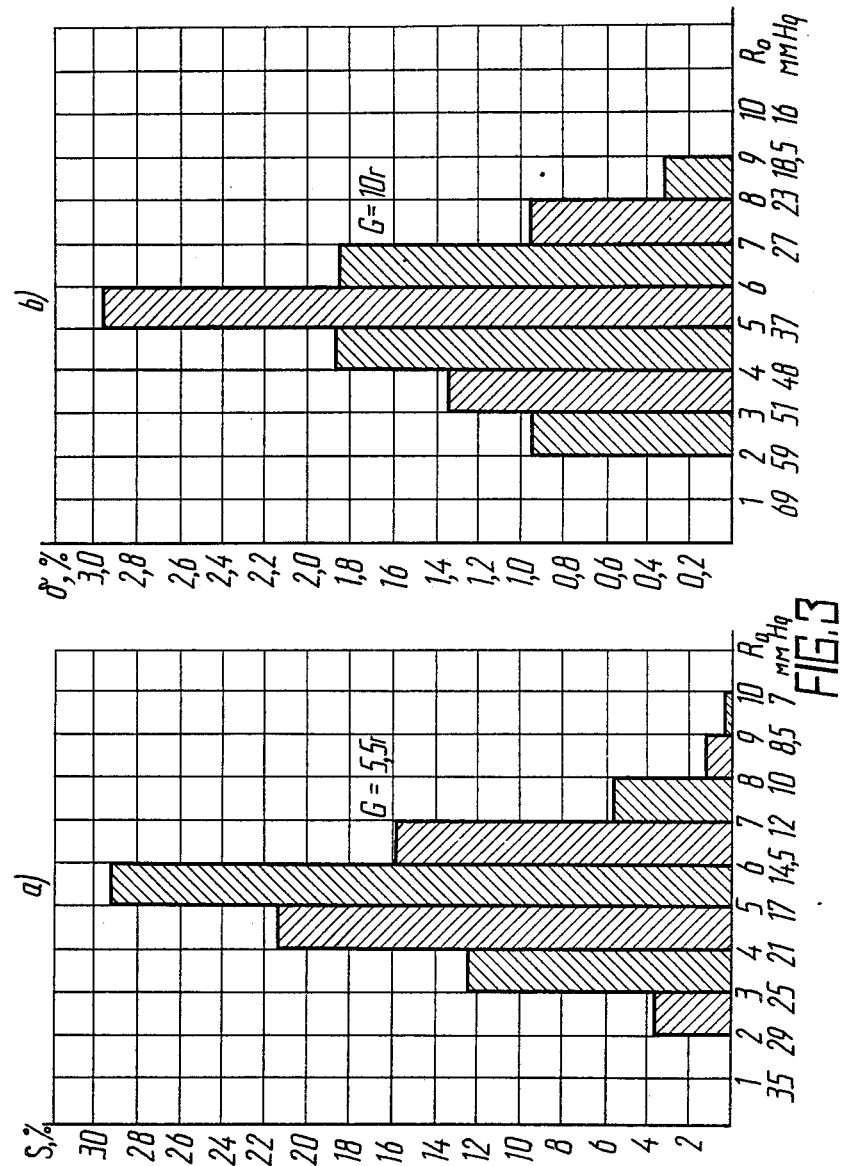
FIGS. 3a and 3b are graphs, showing histograms representing the results of processing the experimental findings obtained from tonography of out-patients.

FIG. 3 represents histograms obtained from processing six thousand experimental tonographic findings taken from out patients. The aforesaid findings are obtained using the standard tonographic precedure and standard tonometer. It has been found that tonograms taken with the plunger weight of 10 g occur about ten times less frequently than those with the plunger weight of 5.5 g, whereas no tonograms with the plunger weight of 7.5 g are encountered altogether. It can be inferred, on the grounds of the data represented in FIGS. 2 and 3, that 96 percent of the tonometric procedures feature the measurement accuracy within 10 percent, the approximation of the pressure relationship being expressed as follows:

$$P_o = A_2 / R_o \qquad (2^{II})$$

The studies carried out also give evidence that the coefficient $A_o$ selected from the root-mean-square relationship gives the similar results. In addition, reduction of the margin 8 of error to 5 percent (FIG. 2) demonstrates that 91 percent of measurement results in case of out-patient examinations fall within that margin of error. It is by appropriately varying the mass of additional load-weights that one seeks for a 100-percent pressure measurement in the margin 7 or 8.

Similar results are obtained from examination of glaucoma patients, but are not herein considered for the sake of simplification of the present disclosure.

Thus, it may be considered to be proven that the value of $P_o$ of intraocular pressure in millimeters of mercury is inversely proportional, within an allowable error, to the length of travel of the plunger of the transducer measuring linear motions $R_o$, that is $$P_o = A_2 / R_o \qquad (2^{II})$$

Therefore when use is made of a frequency-output linear-motion transducer featuring a proportional relationship of the frequency 'f' at its output, the length of travel $R_o$ corresponding to intraocular pressure in conventional units is proportional to the measured frequency 'f', whence $$R_o = kf, \qquad (4)$$

where k is the proportionality factor, while the pressure value of P in millimeters of mercury is proportional to the period T of oscillations at the output of the frequency-output transducer, that is, $$R_o = A_2/R_o = A_2/kf = (A_2 k)T \tag{5}$$

Figure 4:
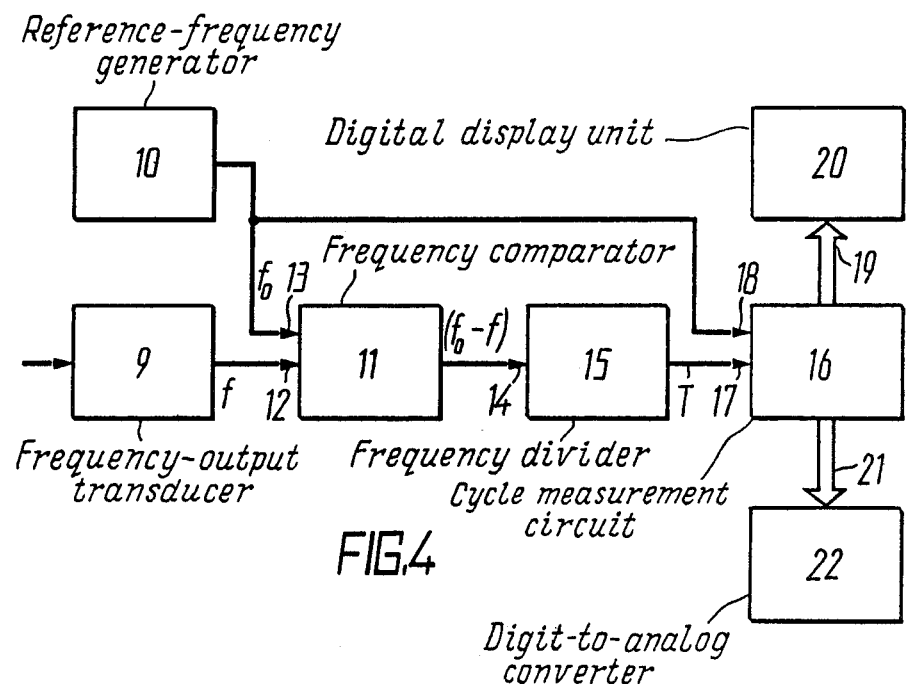
FIG. 4 is a functional block diagram of an ophthalmotonometer, according to the invention.

The mathematical expression (5) points to the direct proportionality of the intraocular pressure measured in millimeters of mercury to the period of oscillations at the output of the frequency-output transducer employed for the pressure measurement, which makes it possible to provide an ophthalmotonometer featuring such a functional diagram that enables intraocular pressure to be measured directly in millimeters of mercury, such a functional diagram being represented in FIG. 4.

The ophthalmotonometer of the invention comprises a frequency-output linear-motion transducer 9, said motions corresponding to intraocular pressure in conventional units, a reference-frequency generator 10, and a frequency comparator 11 to whose inputs 12 and 13 are connected the outputs of the frequency-output transducer 9 and of the generator 10. To the output of the frequency comparator 11 is connected an input 14 of a difference-frequency divider 15.

The tonometer comprises also a circuit 16 for measuring the cycle of the difference-frequency oscillations connected to whose input 17 is the output of the difference-frequency divider 15, while connected to an input 18 thereof is the output of the generator 10.

A signal corresponding to intraocular pressure in millimeters of mercury is applied to the measurement results registering circuit. Used as such a circuit in the herein-considered tonometer is a digital display unit 20 to whose inputs the output of the circuit 16 is connected. The same signal is impressed upon inputs 21 of a digital-to-analogue converter 22 at whose output a signal is registered, corresponding to time-referenced intraocular pressure variation.

Used as the digital display unit 20 and the converter 22 may be any heretofore-known similar device.

FIG. 5 illustrates an elementary electric diagram of the measurement circuit of the ophthalmotonometer under consideration.

The frequency-output transducer 9 comprises an inductor 23 whose inductance varies with the travel of a core 24 associated with a plunger which is adapted to interact with the patient's cornea (omitted in the Drawing) by a widely adopted technique.

The inductor 23 makes part of the oscillatory circuit of a self-excited oscillator 25 built around transistors 26, 27, capacitors 28, 29, 30, 31, 32, and resistors 33, 34, 35, 36, 37, 38 using a heretofore-known pattern, e.g., such illustrated in FIG. 5.

The reference-frequency generator 10 is assembled according to the same electric circuitry as the self-excited oscillator 25 of the frequency-output transducer 9; it comprises an inductor 39, a trimmer 40, transistors 41, 42, capacitors 43, 44, 45, 46, 47, and resistors 48, 49, 50, 51, 52, 53.

The frequency comparator 11 comprises diodes 54, 55 connected to a junction point 56 of which through resistors 57 and 58 are the outputs of the transducer 9 and of the generator 10.

There is provided at the output of the comparator 11 a filter 59 adapted to discriminate the difference frequency and built around a reactor 60, capacitors 61, 62 and a resistor 63.

Connected to the output of the filter is an amplifier 64 based on transistors 65, 66, capacitors 67, 68, 69, 70, 71 and resistors 72, 73, 74, 75, 76, 77, 78.

The difference-frequency divider 15 is made up according to any of the heretofore-known and widely adopted techniques, e.g., can be based on flip-flops 78, while the cycle measuring circuit 16 is made as any counter of pulses of the reference frequency produced by the generator 10. The counting time corresponds to the cycle being measured.

The division ratio 'm' of the frequency divider 15 is calculated according to the following relation:

$$m = (A_2 \cdot n)/f_o, \tag{6}$$

where n is the conversion ratio of the transducer 9 expressed in Hz/conventional unit; and $f_o$ is the frequency of the generator 10.

The ophthalmotonometer operates as follows.

The plunger of the transducer 9 placed on the patient's cornea is urged to assume a certain position with respect to the casing under its own mass and the mass of the additional load weight, the sum of which equals the value of G. The plunger motion is converted into a proportional change of the frequency 'f' of the self-excited oscillator 25. The frequency 'f' is the compared with the frequency $f_o$ of the generator 10 in the comparator 11. A signal next appears at the output of the comparator 11, proportional to the difference frequency $\Delta f = f_o - f$ (7), which is divided, with the division ratio 'm', by the frequency divider 15. Thereupon the cycle T of the difference frequency oscillations is measured in the circuit 16 by counting the number of pulses delivered by the reference-frequency generator 10 for a full oscillation cycle of a signal coming from the output of the divider 15. The measurement result represented in the digital form is displayed by the digital display unit 20 on a light panel. The same result converted into a d.c. signal by the converter 22 is written down by a known technique on any of the heretofore-known recording devices.

The ophthalmotonometer proposed herein measures true intraocular pressure in millimeters of mercury.

Tonometric procedure has been carried out in 25 patients (41 eyes) suffering from glaucoma, in persons suspected of glaucoma, in postoperative patients and in children. The patients were aged from 3 to 78. Intraocular pressure in the patients ranged within 5 to 35 mm Hg. All the patients noted good toleration of the examination carried out.

The examination findings are tabulated in Table II.

The ophthalmotonometer of the invention satisfies fully the requirements imposed by medical practice, is simple in handling and reliable in operation, cuts down the examination time considerably, and is economically efficient. In addition, the instrument is free from contraindications for use and is indispensable in carrying out preventive population screening.

The present invention makes it possible to obtain the results of intraocular pressure measurements directly in millimeters of mercury. Moreover, it is instrumental in attaining higher reading accuracy of the pressure measured due to an averaged initial measurement section, as well as in higher accuracy of measuring some other parameters, such as hydrodynamic coefficients, since their calculation involves greater differences between the initial and final pressure values due to the fact that the values are expressed in milimeters of mercury rather than in conventional units.

TABLE II

| No. | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| 1. | Prior-art tonometer-tonograph, mm Hg | 15.2 | 23.4 | 21.1 | 22.7 | 16.5 | 15.7 | 17.4 | 25.3 | 12.7 | 16.9 | 17.3 | 21.6 | 24.8 | 19.3 |
| 2. | Tonometer of the here-in-proposed construction, mm Hg | 14.2 | 23.6 | 20.8 | 21.9 | 15.8 | 15.0 | 16.9 | 26.1 | 12.1 | 16.1 | 16.2 | 20.1 | 23.1 | 18.6 |
| 3. | Prior-art tonometer-tonograph, mm Hg | 26.4 | 16.3 | 31.3 | 15.6 | 19.3 | 14.7 | 17.5 | 35.9 | 20.2 | 17.3 | 15.8 | 23.4 | 21.2 | 17.9 |
| 4. | Tonometer of the here-in-proposed construction, mm Hg | 27.0 | 15.4 | 32.5 | 14.7 | 18.6 | 13.6 | 17.1 | 33.8 | 18.8 | 16.7 | 14.9 | 24.0 | 22.1 | 16.2 |
| 5. | Prior-art tonometer-tonograph, mm Hg | 11.2 | 17.4 | 16.1 | 15.9 | 17.6 | 20.4 | 18.3 | 22.3 | 15.9 | 17.4 | 16.3 | 14.2 | 13.6 | — |
| 6. | Tonometer of the here-in-proposed construction, mm Hg | 12.1 | 17.1 | 15.2 | 16.2 | 16.9 | 21.0 | 17.6 | 22.0 | 15.1 | 18.2 | 17.0 | 12.9 | 12.2 | — |

What is claimed is:

1. An ophthalmotonometer, comprising:
a reference-frequency generator having an output;
a frequency-output transducer of linear motions which correspond to intraocular pressure having an electric output;
a frequency comparator having a first input connected to aid output of said reference-frequency generator, a second input connected to said electric output of said frequency-output transducer, and an output at which a signal is shaped proportional to a difference between frequencies of the signals produced by said reference-frequency generator and said frequency-output transducer;
a difference-frequency divider having an input connected to said output of said frequency comparator, and an output;
a circuit for measurement of the cycle of difference-frequency oscillations having a first input connected to said output of said difference-frequency divider, a second input connected to said output of said reference-frequency generator, and an output at which a signal is shaped corresponding to intraocular pressure in millimeters of mercury; and
a measurement results registration circuit having an input connected to said output of said measurement circuit.

* * * * *